(12) United States Patent
Rida et al.

(10) Patent No.: US 9,132,422 B2
(45) Date of Patent: Sep. 15, 2015

(54) FLUIDIC INTERFACING SYSTEM AND ASSEMBLY

(75) Inventors: Amar Rida, Chavannes-Remens (CH); Thierry Varidel, Ecublens (CH)

(73) Assignee: Spinomix, S.A., Lausanne (CH)

( * ) Notice: Subject to any disclaimer, the term of this patent is extended or adjusted under 35 U.S.C. 154(b) by 0 days.

(21) Appl. No.: 13/700,644

(22) PCT Filed: Jun. 3, 2011

(86) PCT No.: PCT/IB2011/052440
§ 371 (c)(1),
(2), (4) Date: Jun. 26, 2013

(87) PCT Pub. No.: WO2011/151804
PCT Pub. Date: Dec. 8, 2011

(65) Prior Publication Data
US 2013/0267015 A1  Oct. 10, 2013

(30) Foreign Application Priority Data

Jun. 3, 2010  (CH) .......................... 885/10

(51) Int. Cl.
*B01L 3/00* (2006.01)
*G01N 33/543* (2006.01)

(52) U.S. Cl.
CPC .... *B01L 3/502715* (2013.01); *G01N 33/54326* (2013.01); *B01L 3/50825* (2013.01); *B01L 2200/027* (2013.01); *B01L 2200/0689* (2013.01); *B01L 2300/0672* (2013.01); *B01L 2300/0887* (2013.01); *B01L 2300/123* (2013.01); *B01L 2400/0487* (2013.01); *B01L 2400/0655* (2013.01)

(58) Field of Classification Search
CPC .......... B01L 3/502715; B01L 3/50825; B01L 220/027
See application file for complete search history.

(56) References Cited

U.S. PATENT DOCUMENTS

| 6,664,104 | B2 | 12/2003 | Pourahmadi et al. |
| 6,783,736 | B1 | 8/2004 | Taylor et al. |
| 6,818,185 | B1 | 11/2004 | Petersen et al. |
| 6,893,879 | B2 | 5/2005 | Petersen et al. |
| 2002/0124896 | A1 | 9/2002 | O'Connor et al. |
| 2008/0038714 | A1 | 2/2008 | Gao et al. |
| 2008/0153096 | A1 | 6/2008 | Witty et al. |

FOREIGN PATENT DOCUMENTS

| WO | WO-2008007270 A2 | 1/2008 |
| WO | WO-2008010111 A2 | 1/2008 |
| WO | WO-2008030433 A2 | 3/2008 |
| WO | WO-2010118427 A1 | 10/2010 |

*Primary Examiner* — Sam P Siefke
(74) *Attorney, Agent, or Firm* — Cooley LLP; Ivor R. Elrifi; Christina K. Stock

(57) ABSTRACT

A fluidic assay system assembly comprising: (a) a disposable fluidic cartridge (1) comprising at least one reaction chamber (3) connected to a network of fluidic channels (2) with at least one inlet channel and one outlet channel. The said inlet and outlet channels end at the down side of the fluidic cartridge with at least two connecting pores (4), (4'); (b) a disposable vessel (5) comprising a connection tube (22) immersed in a sample container (6) and ended at the cap of the vessel with an external connection pore (7); (c) a fluidic manifold (8) that is interdependent with the bulk system (12) comprising a fluidic network connected (9) to active fluidic parts (10), (11). The said channel network ends at the top side of the fluidic manifold with at least one connecting pore (13). Wherein the first and the second pores of the fluidic cartridge are interfaced by direct physical contact with the sample container and the manifold pores, respectively.

11 Claims, 8 Drawing Sheets

FLUIDIC INTERFACING SYSTEM AND ASSEMBLY

RELATED APPLICATIONS

This application is a national stage application, filed under 35 U.S.C. §371, of International Application No. PCT/IB2011/052440, filed Jun. 3, 2011, which claims priority to Swiss application No. 00885/10, filed Jun. 3, 2010, which is incorporated herein, by reference, in its entirety.

FIELD OF THE INVENTION

The invention relates to a system for conducting an automated assay on a specimen which contains specific biological or chemical substances that need to be detected. More specifically, the invention discloses a device that includes a fluidic cartridge and the interfacing of the said cartridge with the sample and the different reagents used in performing such assay.

BACKGROUND OF THE INVENTION

The testing of diverse sample types derived from human, animal, plant sources, food and environmental samples plays a crucial role in modern medical diagnosis and treatment, forensic medicine, food safety, industrial processing among many other fields. However, such analyses are very often related to complex processes that relate to labor-intensive, chemical, biological and physical steps on a fluid sample that will end in the detection of specifically targeted molecules or analytes using optical, electrical and biochemical procedures. In the current state-of-the-art, sample analysis steps remain mainly dominated by complex, large and expensive "robotic" instruments operated by expert technicians in centralized laboratories. Consequently, any technology that would automate the complex reaction and sample processing steps while making them more affordable and less space-consuming would address unmet needs for simple, cost-effective assaying solutions.

As an emerging alternative to the robotic platforms, fluidic or microfluidic technologies open new perspectives in assay processing and automation. In relation to recent developments in molecular biology, nanotechnology and optics, (micro)fluidic based systems comprehend indeed the potential of providing integrated solutions, where all steps from sample preparation and assay processing to signal amplification and detection of multiple targets will be integrated in a fully automated, compact cartridge.

A typical example of a commercially available cartridge-based solution is the GeneXpert molecular diagnostics platform from Cepheid (CA, USA) (http://www.cepheid.com) which realized an advance in fully automated molecular testing from sample input to result reporting. As for instance disclosed by the U.S. Pat. No. 6,893,879, U.S. Pat. No. 6,664,104, U.S. Pat. No. 6,818,185 and U.S. Pat. No. 6,783,736, the Cepheid system demonstrates the integration of micro-fabricated chips and other miniaturized fluidic or analytical components in a cartridge type where steps from the separation of a desired analyte from the original sample fluid sample to assay processing and target detection are being performed.

Beyond the integration capabilities, one fundamental issue of the development of a micro-fluidic based system is the interfacing of the fluidic part which is substantially small and compact as compared to the relatively large macro-environment, as defined by the user samples, reagents and sensing elements.

With this respect, the international Pat. Application WO 2008/030433 for instance describes the use of a cartridge, which is adapted to contain samples and reaction fluids to interface with a micro-fluidic chip for use for DNA analysis tests and other assays performed within the micro-fluidic chip. The microfluidic interface is assured through access ports in connection with microfluidic channels and located on the top side of the associated micro-fluidic chip. The reagents and samples contained in external chambers within a fluidic cartridge are dispersed into the microfluidic chip through nozzles that will be brought in communication with the access ports on top of said microfluidic chip. Within the same spirit, WO 2010/118427 discloses a fluidic interface device that includes a cartridge with microfluidic configuration that is in fluid communication with a microfluidic chip through contact pores.

The state-of-the-art coupling and interfacing of the microfluidic based system with the external environment systems, are facing however a real challenge: The integration of maximum functionalities within the micro-fluidic cartridge which leads to a complex and costly "disposable" cartridge or to lower integration properties at the cartridge level resulting in a more complex interfacing device that practically end in complex robotic platforms. The optimal balance between the cartridge complexity/simplicity versus the corresponding interfacing system simplicity/complexity is still an open mostly unresolved issue.

In knowledge of these shortcomings the current invention concerns a system for conducting automated assays within a fluidic cartridge and its interfacing device on a sample containing specific biological or chemical substances that need to be detected. This disclosed system overcomes various limitation and constraints by assuring the simplicity of both the disposable cartridge and its interfacing system.

SUMMARY OF THE INVENTION

The present invention provides a system for the automated procedure of bio-chemical assays that includes:
  a. A disposable fluidic cartridge comprising at least one reaction chamber connected to a network of fluidic channels with at least one inlet and one outlet channels, wherein the said inlet and outlet channels end at the down side of the fluidic cartridge with at least two connecting pores;
  b. A disposable vessel comprising a connection tube immersed in a sample container and ended at the cap of the vessel with an external connection pore;
  c. A fluidic manifold that is interdependent to the bulk system comprising a fluidic network connected to active fluidic parts, wherein the said channel network ends at the top side of the fluidic manifold with at least one connecting pore; and
wherein the first and the second pores of the fluidic cartridge are interfaced by direct contact with the sample and the manifold container pores respectively.

The key advantage of this invention is the simplicity of the automated system in managing the sample as well as the different reagents that will be used in any assay process.

This simplicity is first translated by the fluidic cartridge design that can be composed from plastic molded parts preferably comprising of a structured layer with fluidic structures and of a sealing layer. In a preferred realization of the invention, the closing-down layer is composed of an elastomeric material which in practice will serve as an interface to seal the connection of the fluidic cartridge pores with the respective pores of the disposable vessel and fluidic manifold.

Accordingly, the present invention discloses a fluidic cartridge for assaying target biomolecules or particles from a crude sample, the cartridge comprising of:
  d. at least one structure top layer containing:
    i. a reaction chamber with a solid support that is designed to capture the said target biomolecules,
    ii. a first inlet and outlet channels that are in fluid communication with the said reaction chamber and that will be used to bring the sample it and out the reaction chamber,
    iii. a second inlet and outlet channels connected to the said reaction chamber and will be used for eluting the purified biomolecules,
    iv. wherein the second inlet and outlet channels are diverging branch of the first inlet and outlet channels,
  e. a closing down layer composed from a flexible material and comprising connection pores associated to the ends of the said inlets and outlets channels, Further, the simplicity of the automated system is realized by handling the sample to be assayed within a disposable sample vessel container from a traditional laboratory sample collection tube with a pierceable cap. To assure the connectivity with the fluidic cartridge a syringe adapter is inserted into the tube. Such tubes will be preferably used for containing the starting sample that will be assayed and thereby avoid the complexity induced by the integration of sample storing directly into the fluidic cartridge.

Further, the simplicity of the automated system is realized by a fluidic manifold that comprises fluidic network channels and active fluidic elements like valves and pumps mounted on the said manifold. The fluidic manifold according to the invention is further characterized by the fact that it is part of the bulk system. Fluidic connectivity of the fluidic manifold with the disposable fluidic cartridge is assured through connection pores disposed on the top side of the manifold and that will be directly in contact with the fluidic cartridge and the pores reflectively. Furthermore, the fluidic manifold comprises connection pores that will be in a fluidic communication with the diverse assaying reagents. The latter will be transported through the fluidic manifold network channels to be thereafter injected into the fluidic cartridge through a specifically dedicated pore. To avoid cross contamination, the manifold fluidic network channels are divided into a first network segment of channels specifically designed to handle the sample to be assayed and a second segment of channels specifically designed to handle the reagents and wherein the said first and second segment of channels are fluidically disconnected from each other.

In summary, the current invention discloses a fluidic system assembly for conducting bio-assays comprising of:
  (1) A fluidic cartridge plastic element in which the assay will be conducted. Without any active element integration, this disposable element can be easily manufactured using standard plastic injection molding and assembling techniques. Designed for specific assays, the cartridge can further include assay specific reagents as specific affinity or detection reagents preferably in a lyophilized format.
  (2) A sample container and handling vessel that must be also disposable to avoid any cross-contaminations. Rather than to be directly integrated into the fluidic cartridge, the sample container according to the invention is a standard laboratory tube with a pierceable cap. To assure the fluidic connectivity, preferably, a syringe adapter is inserted in the tube through the said pierceable cap.
  (3) A fluidic manifold that contains the system active elements (valves, pumps, actuation and sensing elements) will be integrated. This part of the system is not disposable and will be considered as part of the bulk of the system. The fluidic manifold can also directly integrate the generic reagents handling to avoid cross contamination issues.
  (4) The manifold as well as the sample containers will be directly interfaced with the fluidic cartridge through the respective pores disposed at the down layer of the said fluidic cartridge. The fluidic manifold can also serve as support to receive the sample vessels. The microfluidic chip will be on the top of the fluidic manifold and the sample vessel to provide the full fluidic sealed assembly.

BRIEF DESCRIPTION OF THE DRAWINGS

The objects and features of the present invention are set forth with particularity in the appended claims. The present invention, both as to its organization and manner of operation, together with further objects and advantages, may best be understood by reference to the following description, taken in connection with the accompanying drawings, wherein

DETAILED DESCRIPTION OF THE PREFERRED EMBODIMENTS

Figure 1:
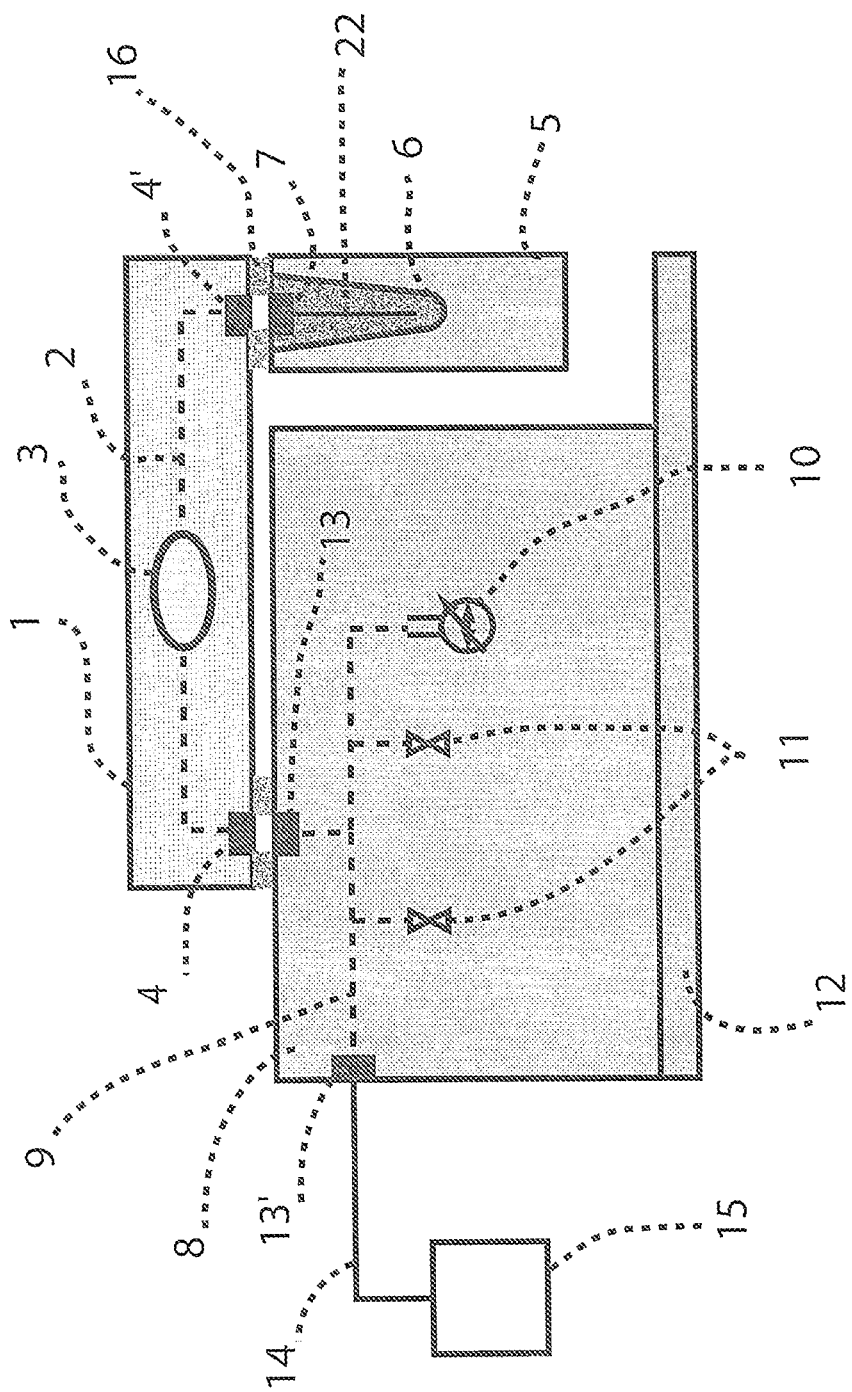
FIG. 1 is a schematic representation of the fluidic assembly and samples interfacing according to a preferred embodiment of the invention.

The main purpose of the present invention is an automated system for sample handling, preparation and assaying using a disposable of a simple designed and low cost fluidic cartridge. Furthermore, the invention discloses an interfacing system of the said cartridge with the sample to be assayed and also with the reagents used in performing such assay. Another main attainable objective of the present invention is a fully automated device for biological liquid sample and reagent processing in a microfluidic using the said fluid cartridge and the related interfacing system.

In general, the microfluidic environment of the invention concerns devices typically designed at a scale suitable to analyze micro-volumes preferably in the range 0.1 ml to 500 µl. However, for one of the major applications of the invention large sample sizes are used to concentrate specific biomolecules or biological cells or particles in the device to a small volume for subsequent analysis. The microscale flow channels and wells have preferred depths and widths in the order of 0.05-1 mm. The "reaction chamber" that is part of the microfluidic network as used herein refers to chambers with a cavity that have a volume in the range of 1 µl to 1 ml and preferably in the range 10 µl to 200 µl. However, for many applications, larger "mesoscale" dimensions in the scale of millimeters may be used. Similarly, geometry features often will have larger dimensions than the microchannels, in the scale of 1-10 mm width and 1-5 mm depth.

The disclosed system and devices herein can be applied to perform complex assays used in various testing laboratories and clinical procedures. Such procedures can include but are not limited to extraction, purification and concentration of target molecules or particles from a wide range of target substances in biological samples. Examples of target substances are cells, cell components, cell subpopulations (both eukaryotic and prokaryotic), bacteria, viruses, parasites, antigens, specific antibodies, nucleic acid sequences and the like. Furthermore, such assay procedures can include the steps without limitation of labeling, amplifying and detecting such target molecules or particles. In particular, detection procedures including, but not limited to polymerase chain reaction (PCR), real-time PCR, ligase chain reaction (LCR), strand displacement amplification (SDA), and nucleic acid sequence based amplification (NASBA).

The present invention provides a system for automated performance of bio-chemical assays that includes a disposable fluidic cartridge (1) comprising of at least one reaction chamber (3) connected to a network of fluidic channels (2) with at least one inlet and one outlet channel. The said channels end at the down side of the fluidic cartridge with at least two connecting pores (4), (4').

This simplicity is first translated into the fluidic cartridge design that can be composed from a plastic molded parts comprising, as shown in FIG. 1, from at least one layer 1(a) with fluidic structures and a sealing layer 1(b). In a preferred realization of the invention, the closing down layer is composed from a flexible polymeric material. With this respect, the flexible closing layer is preferably composed from an elastomer and more preferably from a thermoplastic elastomer. For the fluidic cartridge working, the said flexible polymeric material forming the lower side of the fluidic cartridge will further serve as an interface (16) to seal the connection of the fluidic cartridge pores (4'), (4) with the respective pores of the disposable vessel (7) and fluidic manifold (13).

Figure 2:
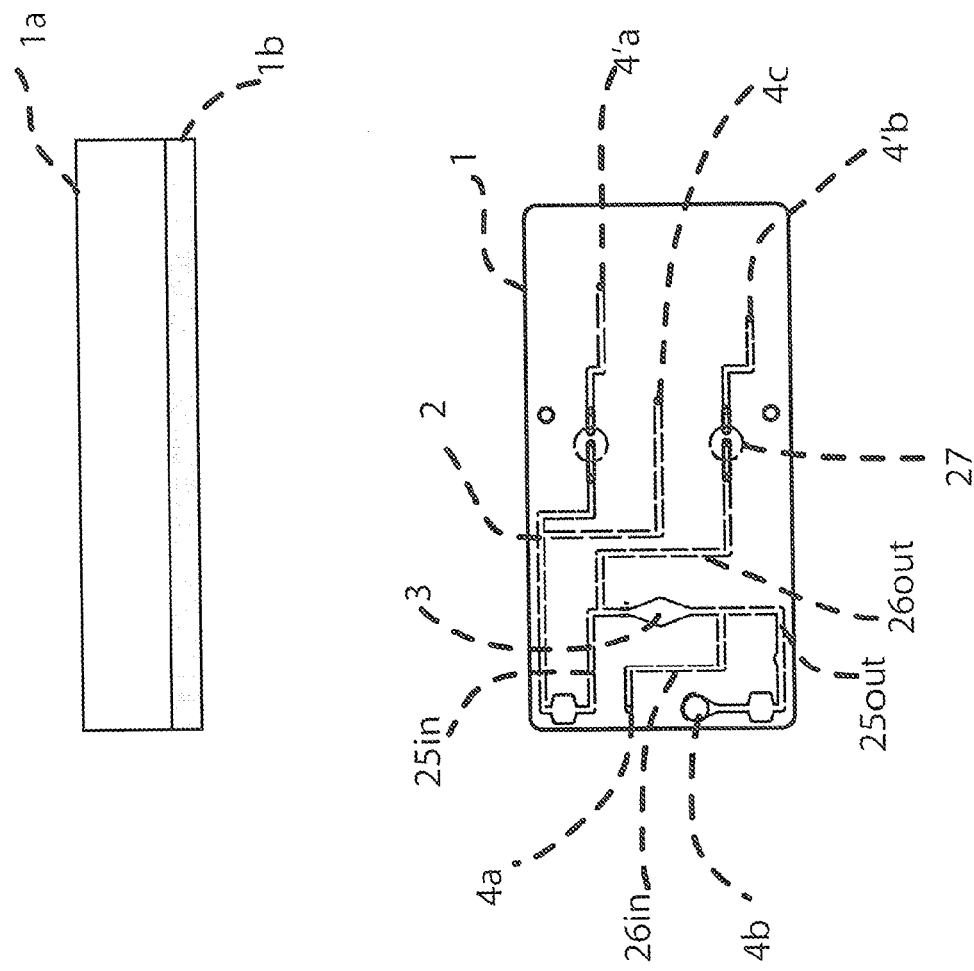
FIG. 2 is a schematic representation of the fluidic cartridge according to a preferred embodiment of the invention.

The structured layer of the fluidic cartridge 1(a) comprises the fluidic network and the reaction chamber according to the invention. The layout of a preferred realization of such structured layer is shown in FIG. 2. The structured layer is composed from a fluidic channel network (2) connected to a reaction chamber (3). This connection is operated through an inlet and outlet channel (25in) and (25out) respectively. The fluidic channel network ends at the down sides of the chips in connection pores (4).

Operation of the fluidic cartridge as shown in FIG. 2 consists of aspirating the sample within the sample vessel (5) connected to the pore (4'a), into the reaction chamber (3) through the inlet channel (25in). This is achieved using an active pump connected to the outlet channel (25out) through a connection pore (4b). After being processed in the reaction chamber, the sample can be transferred to a waste container (15) connected to the manifold through a connection pore (13') as shown in FIG. 1.

Figure 3:
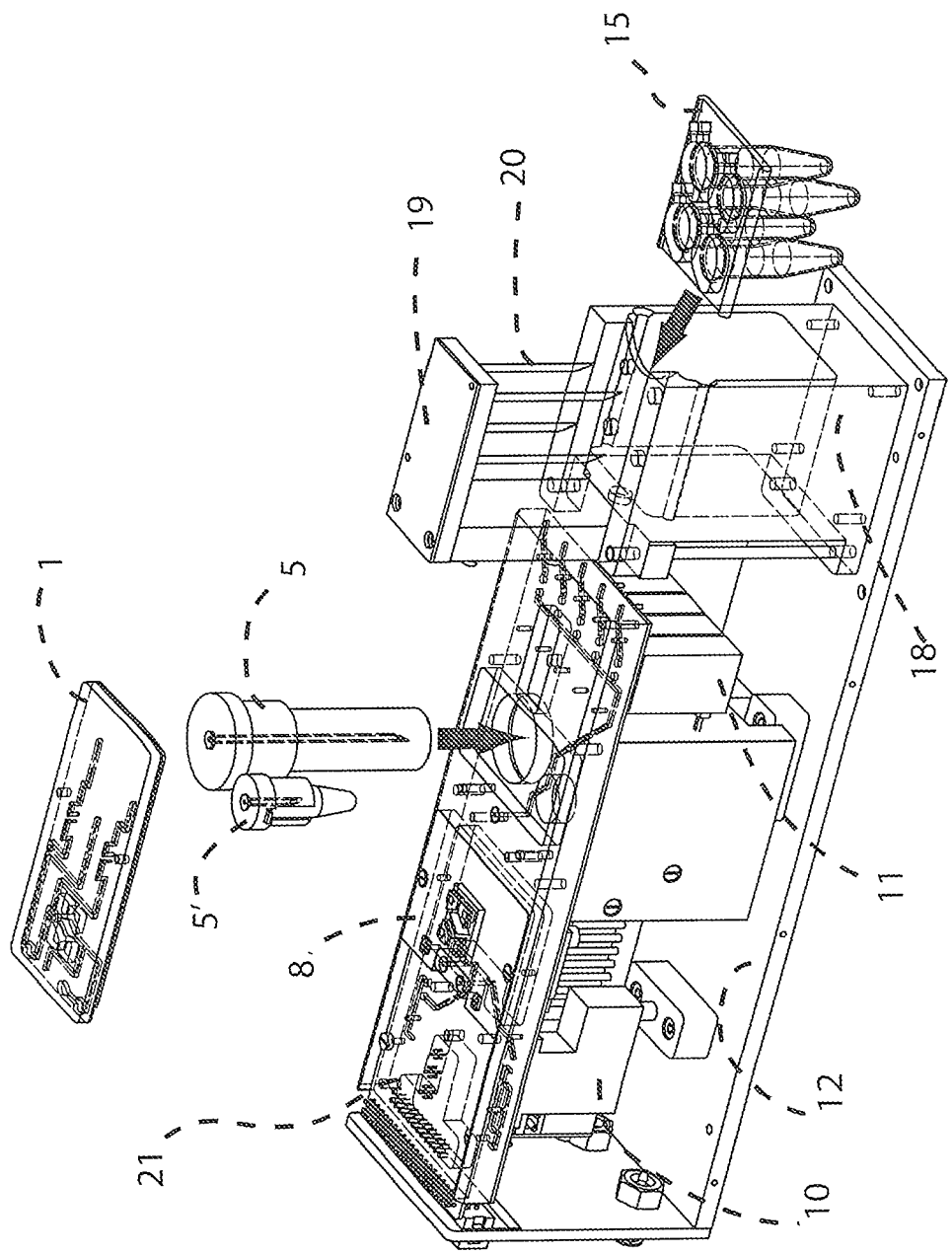
FIG. 3 shows a schematic view of a system realization that includes the key features of the invention. The system design, components and the connectivity of such components are shown in accordance with the preferred embodiments of the invention.
Figure 4:
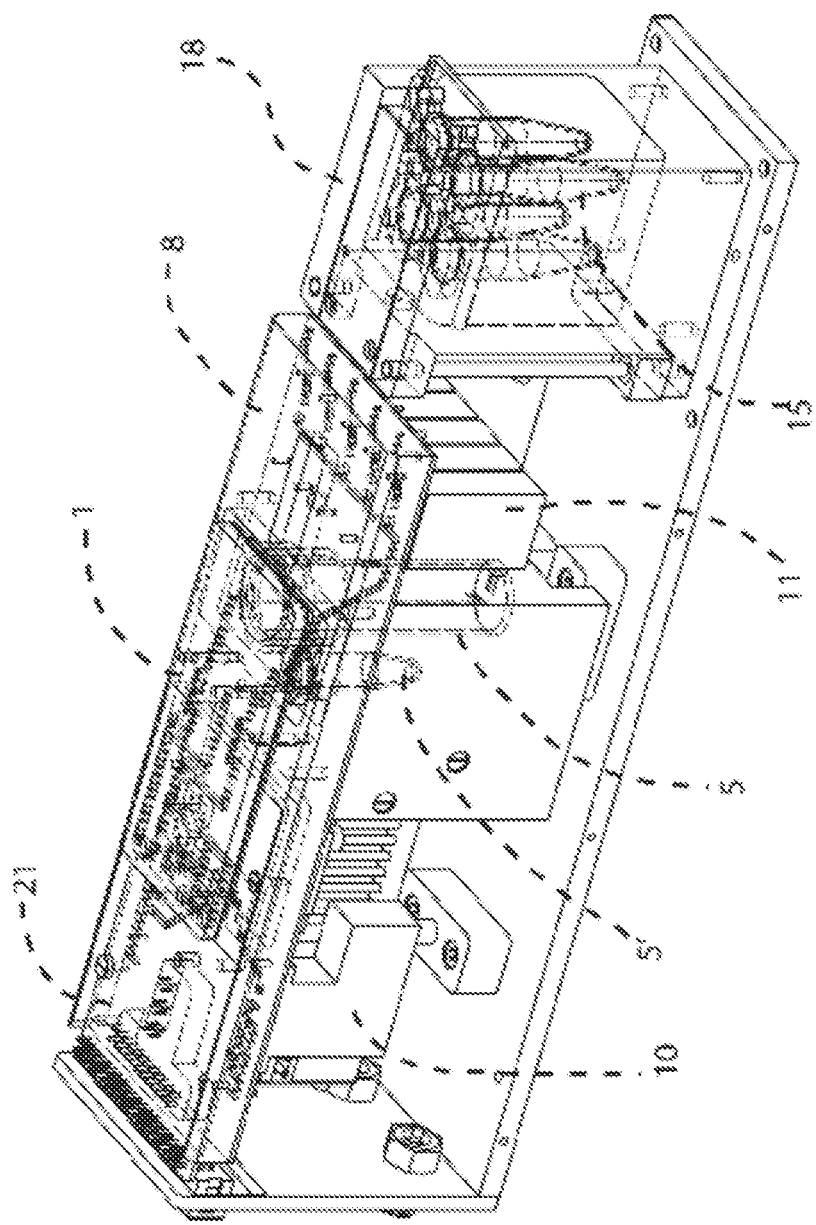
FIG. 4 shows a schematic representation of the system of the FIG. 3 after the different components of the system have been assembled.

The fluidic cartridge according to another preferred embodiment of the invention further comprises a second sample connection pore (4'b) connected to the reaction chamber (3) through a second outlet channel (26out). The second outlet channel (26out) forms a diverging branch of the first inlet channel (25in). In operating conditions, the connection pore (4'b) is directly connected to a recovery sample vessel (5') (as shown in FIG. 3) that will be used to recover the reaction product(s) from the reaction chamber through the outlet channel (26out). This can be assured by pushing air using a second active pump element connected to a second inlet channel (26in) of the reaction chamber through a second connection pore (4a) and wherein the said second inlet channel (26in) forms a diverging branch of the first outlet channel (26out). As a typical example, but not limited to, the recovered material can comprise purified bio-molecules as nucleic acids or proteins.

The fluidic cartridge according to the invention further comprises an injection pore (4'c) through which different generic reagents, like but not limited to washing, lysis, binding or detection reagents, can be transferred to the reaction chamber by the aspiration pump connected to the pore (4b).

According to a preferred embodiment of the invention, the reaction chamber contains a solid support with an active surface to attach or capture target molecules or particles carried by the sample. The said solid support includes but not limited to particles (preferably magnetic) or porous matrix.

From the preceded, the invention discloses a fluidic cartridge for purifying target biomolecules from a sample that comprises:

(a) at least one structure top layer containing:
i. a reaction chamber (3) with a solid support that is designed to capture the said target biomolecules,
ii. a first inlet (25in) and outlet (25out) channel that are in fluid communication with the said reaction chamber and that will be used to bring the sample into and out of the reaction chamber,
iii. a second inlet (26in) and outlet (26out) channel connected to the said reaction chamber and that will be used for eluting the purified biomolecules
iv. wherein the second inlet and outlet channels are diverging branches of the first inlet and outlet channels,
(b) a closing down layer composed from a flexible material and comprising connection pores associated to the ends of the said inlet and outlet channels.

In a preferred embodiment, the closing down layer of the fluidic cartridge further can be used as an elastic membrane (27) that can be deformed using an external actuation to seal one specific channel and thereby prevent the flow through the said channel. This is particularly important in operating the chip, where by using this valve mechanism it allows for instance to seal the recovery channel (26out) or the sample inlet channel (25in) during the sample aspiration out of the sample tube (5) into the reaction chamber (3) or the eluate sample recovery from this reaction chamber into the recovery tube (5') respectively.

Accordingly, the present invention further provides a system for automated conducting of bio-chemical assays that includes at least one disposable vessel (5) comprising of a connection tube (22) immersed in a sample container (6) and ending at the cap of the vessel with an external connection pore (7a).

Rather than to be directly integrated into the cartridge, the simplicity of the systems consists of the use a disposable sample vessel container (5) composed from a traditional laboratory sample collection tubes (25) with a pierceable cap (23). To assure the connectivity with the fluidic cartridge a syringe adapter (22) is inserted into the tube. It will be obvious for a person having ordinary skills in the art that the sample containing vessel can be alternatively manufactured as one piece with the connection tube already integrated into the vessel core.

In a preferred embodiment, such tubes will be preferably used for containing the starting sample that will be assayed.

Preferably also, the collection tube according to the invention can be used as a tube (5') for recovering specific molecules as for instance purified bio-molecules or particles after their separation in the fluidic cartridge. In this particular context, the recovery tube can be also used as an intermediary tube that can contain a specific liquid that will further react with the sample after being eluted out of the reaction chamber. Such reaction can include but not limited to, a buffering re-adaptation reaction, enzymatic reaction, target amplification reaction and a detection reaction. Furthermore, after reacting within the said recovery tube, the resulting reactant can further be pumped out into the fluidic cartridge for further assay processing steps.

In a preferred embodiment according to the invention, the automated system assembly for conducting bio-chemical assays can further include at least one disposable vessel (5') ending at the cap of the vessel with an external connection pore (7b) and that can be used for recovering reactants as purified bio-molecules out of the fluidic cartridge. The difference of this tube as compared with the tube according to the preceding embodiments is that the reactant cannot be further pumped out into the fluidic cartridge for further assay processing steps.

Accordingly, the present invention further provides a system for the automated performance of bio-chemical assays that includes a fluidic manifold (8) that is part to the bulk system (12) comprising of a fluidic channel network (9) and active fluidic components (10), (11). The said channel network ends at the top side of the fluidic manifold with at least one connecting pore (13) and wherein the first and the second pore (4'), (4) of the fluidic cartridge are interfaced by direct contact with the sample (7) and the manifold (13) container pores respectively.

Figure 5:
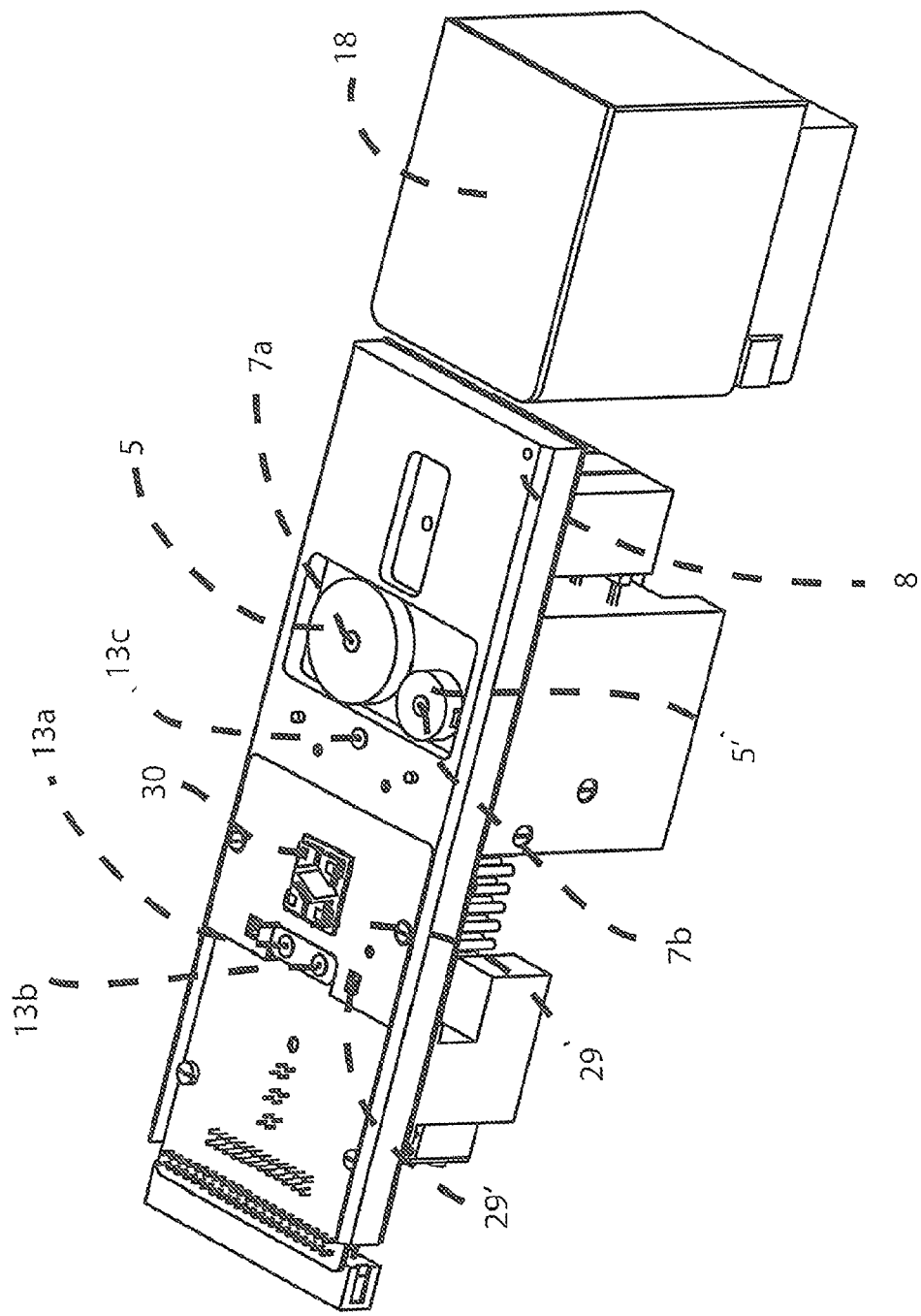
FIG. 5 shows a schematic representation of the system of the FIG. 4 with an emphasis of the disposable vessels and the fluidic manifold assembly according to a preferred embodiment of the invention.
Figure 6:
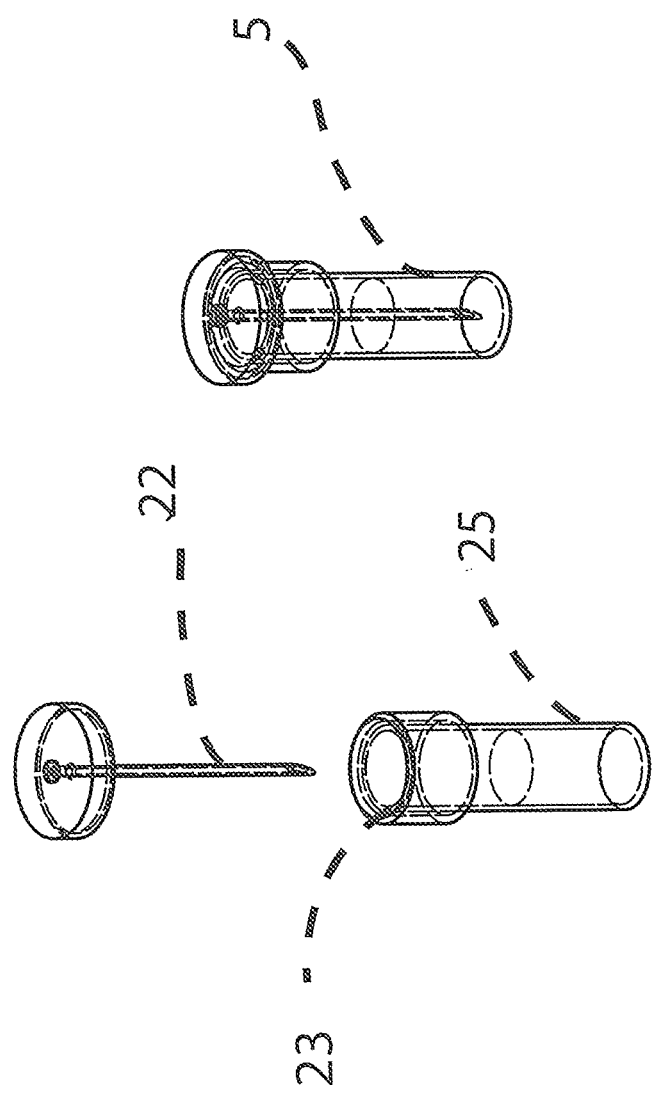
FIG. 6 is a schematic representation of the disposable vessels according to a preferred embodiment of the invention.

In a preferred embodiment, the fluidic manifold (8) comprises of a fluidic network channels (9) and of active fluidic elements like valves (11) and pumps mounted on the said manifold (10). The fluidic manifold according to the invention is further characterized by the fact that it is part of the bulk system (12). Fluidic connectivity of the fluidic manifold (8) is assured through connection pores (13) disposed on the top side of the manifold. The said connection pores (13) are designed in a way to be aligned with corresponding connection pores (4) positioned on the down side of the fluidic cartridge. With this respect and as shown in FIG. 5, the manifold pores (13a), (13b) and (13c) will be respectively connected to the fluidic cartridge (4a), (4b) and (4c). As already described, the connections (13b)-(4b) will assure the functions of aspirating the sample from the vessel (5) to the reaction chamber (3) within the fluidic cartridge (1) while the pore connectivity (13a)-(4a) will be used to recover the reaction products to the vessel (5') by injecting air to pouch the eluate out of the reaction chamber into the recovery tube. Additionally, the connection (13c)-(4c) can be used to inject reagents (like but not limited to washing, lysis, binding, enzymes, buffers . . . ) into the fluidic cartridge and therefore the reaction chamber by the aspiration pump connected to the pore (13b)-(4b). As shown in FIG. 3, the reagents are preferably provided in disposable containers (15) that are in fluidic connection with the manifold.

In a preferred embodiment and as shown in FIG. 3, the reagent disposable containers (15) are first introduced in a locking part (18) composed from a moving part comprising connecting syringes (20) with a supporting fluidic part (19). The supporting fluidic part (19) comprises fluid transfer channels associated with each syringe. Each transfer channel of the fluidic part is connected to the fluidic manifold (8) by classical tubing and fittings (not shown). By that, a series of solenoid valves (11) mounted on the manifold will be used to select one specific reagent that will be transferred from the respective reagent container (15) to the manifold pore (13c) and thereby be injected into the fluidic cartridge (1).

In preferred embodiment, the manifold can not only used as a support to transfer the sample(s) and the reagents into and from the fluidic cartridge but also to inject reagents or recover eluate into the samples vessels (5)-(5'). For instance, a reagent can be injected through the pore connectivity (13c)-(4c) from a reagent container (15) into the fluidic cartridge to be thereafter transferred in a sample vessel (5) or (5').

As described by the different embodiments, the disclosed fluidic assembly permit to perform extremely complex assay procedures and reagents combinations in a very simple overall system design.

Figure 7:
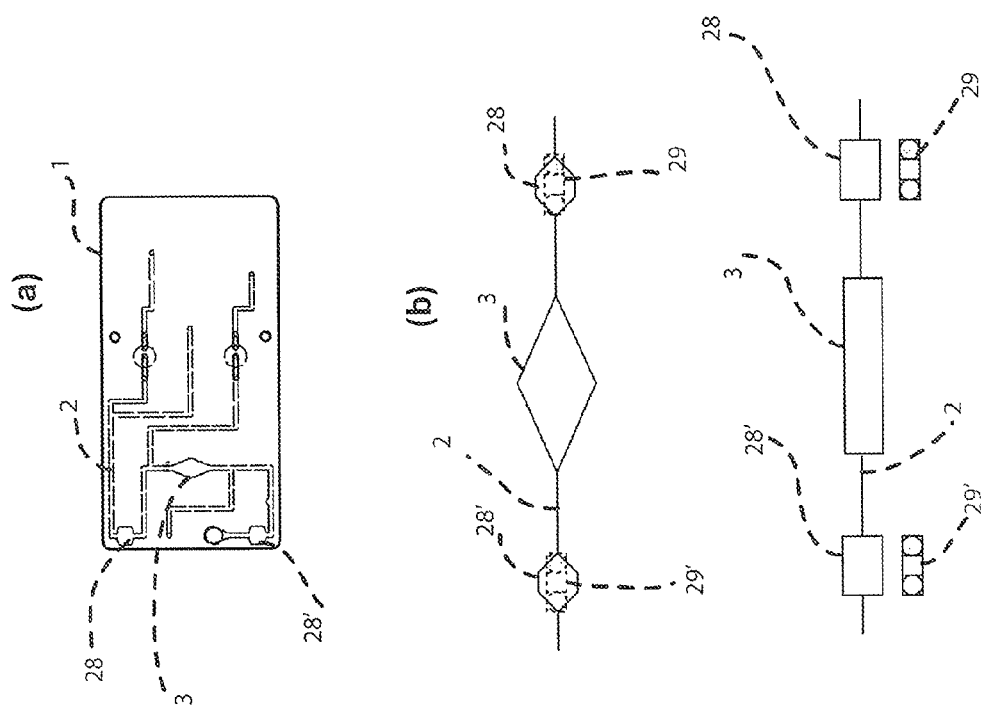
FIG. 7 is a schematic representation of the liquid position sensing which comprises a fluidic cartridge with a reaction chamber and at least one optical sensor positioned on one side of the said reaction chamber.
Figure 8:
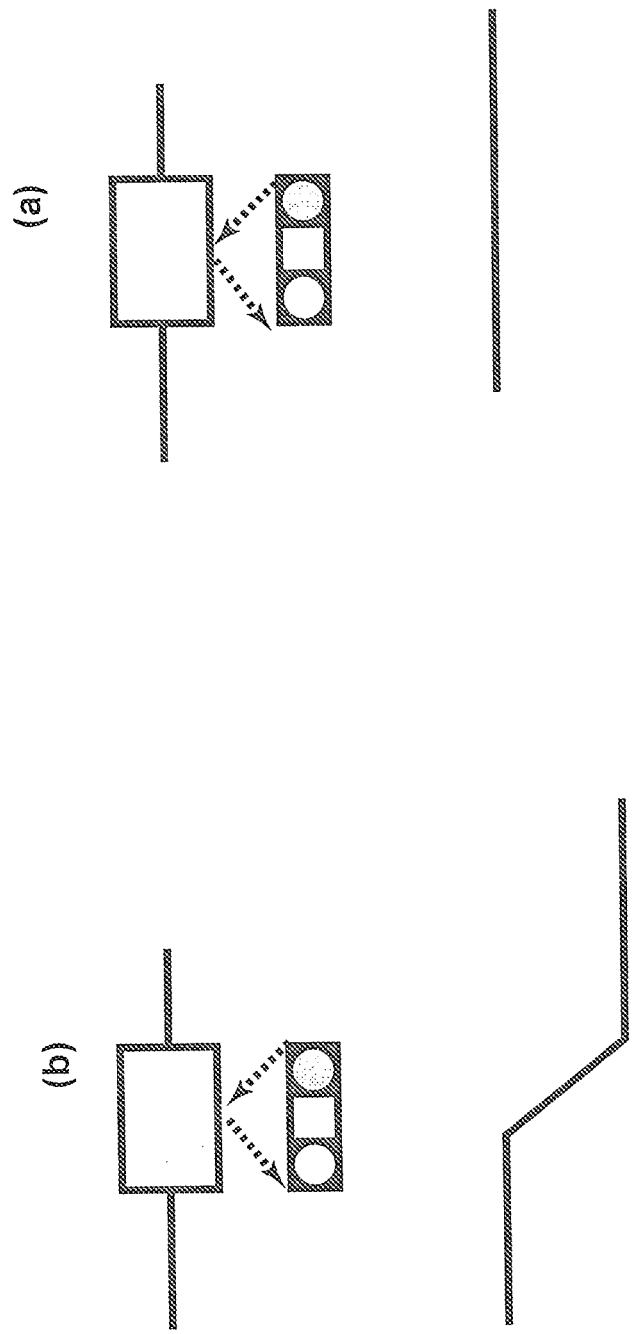
FIG. 8 is schematic representation of the liquid position sensing method according to the invention.

For more precise positioning and control of the different liquids in the reaction cartridge, in a preferred embodiment of the invention, the fluidic manifold further integrates optical sensors (29), (29') as shown in FIG. 5. As illustrated in FIG. 7 the optical sensors will be placed on both side of the reaction chamber (3) facing windows of detection channels (28) and (28'). The role of the optical sensor (29) is to detect the presence of the liquids in the detection windows (28). For that, a standard proximity sensor can be used and that comprises of a photodiode and a laser diode (LED). As shown in FIG. 8, the presence of the liquid in the detection window (FIG. 8b) channel (28) leads to a change in the reflection of the light emitted by the LED when compared with the case liquid absence ((FIG. 8a). This change of the light reflection induces a drop of the signal detected by the photodiode in case the liquid is present in the detection window. This sensing process can be used to determine the position of the liquid upstream and downstream of the reaction chamber, which is very important of the control and management of the assay procedures.

The liquid position according to the invention is particularly required in assays based on magnetic particles where the magnetic particles handling is particularly sensitive to the presence or absence of the liquid. The magnetic particles handling are preferably handled according to the device and the method disclosed in the international patents applications WO2008/010111 and WO2008/007270, incorporated herein as a reference. In fact, when the magnetic particles are homogenously mixed within the reaction chamber it is important to assure that the chamber is fully filled with liquid to avoid an inadequate filling during the process.

From the preceded, the invention discloses a fluidic assembly for conducting bioassays which comprises a fluidic cartridge with a reaction chamber and at least one optical sensor positioned on one side of the said reaction chamber. In the preferred embodiment, the optical sensor is a proximity planar sensor comprising of an emitting Laser diode (LED) and a detection photodiode. Accordingly, the reaction chamber preferably further comprises magnetic particles that serve as a solid support for performing the said bioassays.

The invention claimed is:

1. A fluidic assay system assembly comprising:
   a. a disposable fluidic cartridge comprising at least one reaction chamber, with a solid support that is designed to capture at least one target biomolecule or particle out of a sample, wherein said reaction chamber is connected to a network of fluidic channels comprising:
  i. a first inlet channel and a first outlet channel that are in fluid communication with the said reaction chamber and that are used to bring the sample in and out of the reaction chamber, wherein the said first inlet and outlet channels end at the down side of the fluidic cartridge with at least two respective connecting pores; and
  ii. a second inlet channel and a second outlet channel connected to said reaction chamber that are used for eluting the purified biomolecules or particles out of the reaction chamber wherein the said second inlet and outlet channels end at the down side of the fluidic cartridge with at least two respective connecting pores;
wherein the second inlet and outlet channels are diverging branches of the first outlet and inlet channels respectively, and
  b. disposable sample and recovery vessels, with an external connection pore; and
  c. a fluidic manifold that is interdependent to a bulk system mounted on a bulk system baseplate comprising a fluidic network connected to an active fluidic part, wherein the said network of fluidic channels ends at the top side of the fluidic manifold with at least two connecting pores;
wherein the first connecting pores of the fluidic cartridge, are interfaced by direct contact with the sample vessel pores and the fluidic manifold pores, and the second connecting pores of the fluidic cartridge are interfaced by direct contact with the fluidic manifold pores and the elution recovery vessel pores.

2. The fluidic assay system assembly according to claim 1, wherein the fluidic cartridge comprises at least one layer with fluidic structures and closing down layer composed from a flexible polymeric material.

3. The fluidic assay system assembly according to claim 1, wherein the active fluidic parts connected to the fluidic manifold comprise pumps and valves mounted on said manifold.

4. The fluidic assay system assembly according to claim 1, wherein the fluidic manifold is further in fluidic communication with reagent containing vessels.

5. The fluidic assay system assembly according to claim 1, wherein the fluidic manifold is further in fluidic communication with a waste containing vessel.

6. The fluidic assembly according to claim 1, which comprises a fluidic cartridge with a reaction chamber and at least one optical sensor positioned in one side of said reaction chamber, wherein the at least one optical sensor is used for controlling the liquid positioning with respect to the reaction chamber within the reaction cartridge.

7. The fluidic assay system according to claim 1, wherein in processing, the sample is aspirated through the reaction chamber from the vessel-fluidic cartridge connectivity pore to the manifold-fluidic cartridge connectivity pore.

8. The fluidic assay system according to claim 1, wherein the manifold further comprises a connection port to inject a reagent into the fluidic cartridge through an inlet positioned the down side of the fluidic cartridge.

9. The fluidic cartridge of the fluidic assay system according to claim 1, wherein the solid support within the reaction chamber comprises magnetic particles.

10. The fluidic assay system assembly according to claim 1, wherein the vessels comprise a connection tube immersed in a sample container and ended on the cap of the vessels.

11. The fluidic assay system according to claim 1, wherein in processing, the target biomolecules or particles are eluted from the reaction chamber by pouching air from the manifold-fluidic cartridge connectivity pore to the elution vessel-fluidic cartridge connectivity pore.

* * * * *